(12) United States Patent
Ostergard

(10) Patent No.: US 10,596,023 B2
(45) Date of Patent: *Mar. 24, 2020

(54) ANKLE BRACE

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 564 days.

This patent is subject to a terminal disclaimer.

(21) Appl. No.: 15/368,030

(22) Filed: Dec. 2, 2016

(65) Prior Publication Data

US 2017/0079827 A1   Mar. 23, 2017

Related U.S. Application Data

(63) Continuation-in-part of application No. 13/871,094, filed on Apr. 26, 2013, now abandoned.

(51) Int. Cl.
| | | |
|---|---|---|
| *A61F 5/01* | (2006.01) | |
| *A43B 7/20* | (2006.01) | |
| *A43C 5/00* | (2006.01) | |
| *A43C 1/00* | (2006.01) | |
| *A43B 5/02* | (2006.01) | |
| *A43C 11/00* | (2006.01) | |
| *A43B 3/16* | (2006.01) | |

(52) U.S. Cl.
CPC .............. *A61F 5/0111* (2013.01); *A43B 7/20* (2013.01); *A43B 3/163* (2013.01); *A43B 5/02* (2013.01); *A43C 1/00* (2013.01); *A43C 5/00* (2013.01); *A43C 11/008* (2013.01)

(58) Field of Classification Search
CPC .... A43B 5/02; A43B 7/20; A43B 5/18; A43B 3/163; A61F 5/0111; A61F 13/066; A61F 5/0127; A61F 13/06; A43C 5/00; A43C 11/008
USPC ......... 602/23, 27, 5, 28; 36/88, 89, 11.5, 91, 36/92, 140; 128/882
See application file for complete search history.

(56) References Cited

U.S. PATENT DOCUMENTS

| | | |
|---|---|---|
| 2008/0082034 A1 | 4/2008 | Wilkerson |
| 2008/0306422 A1 | 12/2008 | McChesney et al. |
| 2009/0216167 A1 | 8/2009 | Harris |
| 2009/0247923 A1 | 10/2009 | Lundberg |
| 2012/0302933 A1 | 11/2012 | Ostergard |

*Primary Examiner* — Anna K Kinsaul
*Assistant Examiner* — Caitlin A Carreiro
(74) *Attorney, Agent, or Firm* — Dennis L. Thomte; Thomte Patent Law Office LLC

(57) ABSTRACT

An ankle brace which is positioned on an ankle of a person which incorporates a tensioning structure which permits full range of motion to the ankle joint but which prevents the ankle joint from moving past its normal range of motion to protect the ankle joint.

3 Claims, 6 Drawing Sheets

ANKLE BRACE

CROSS-REFERENCE TO RELATED APPLICATION

This is a Continuation-In-Part Application of application Ser. No. 13/871,094 filed Apr. 26, 2013, entitled ANKLE BRACE which is a Continuation-In-Part Application of application Ser. No. 13/134,087, filed May 27, 2011 entitled ANKLE BRACE.

BACKGROUND OF THE INVENTION

Field of the Invention

This invention relates to an ankle brace and more particularly to an ankle brace including a tensioning system which functionally stabilizes the ankle as it reaches extreme ranges of motion.

Description of the Related Art

Conventional braces for protecting joints of the body do so by restricting or limiting motion of the joint to which it is applied to prevent a new injury or to protect a pre-existing injury. An ankle joint, just like all the joints in the human body, has a natural range of motion that it can move through without causing damage to itself. As it reaches the end of these ranges, the body has structure such as ligaments and tendons to create tension to end range of motion and protect the joint. Many of the prior art ankle braces do prevent the ankle from exceeding its extreme ranges of motion but do not provide the necessary flexibility to permit the athlete to function normally.

Applicant's ankle brace described and shown in the co-pending application represents an improvement in the ankle brace art. The instant invention represents a further improvement in the ankle brace art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An ankle brace is disclosed for use with a cleated athletic shoe having a sole with a lower surface, with cleats extending downwardly therefrom, a lateral side, a medial side, an upper part with an upper end, a lacing closure with upper and lower ends, including a plurality of spaced-apart pairs of eyelets adapted to have a shoe lace threaded therein. The brace of this invention includes a flexible lateral portion having an upper end, a lower end, a forward end, a rearward end, an outer side and an inner side. The upper end of the lateral portion preferably has first, second and third spaced-apart eyelets formed therein at the forward end thereof. The lateral portion also has fourth and fifth eyelets formed therein rearwardly of the third eyelet thereof. An upwardly extending first loop is secured to the upper end of the lateral portion adjacent the eyelets at the forward end thereof. An upwardly extending second loop is secured to the upper end of the lateral portion rearwardly of the first loop. An upwardly extending third loop is secured to the outer side of the lateral portion rearwardly of the second loop. A lateral portion is removably positioned adjacent the lateral side of the upper part of the shoe.

The ankle brace also includes a flexible medial portion having an upper end, a lower end, a forward end, and a rearward end, an outer side and an inner side. The upper end of the medial portion preferably has first, second and third spaced-apart eyelets formed therein at the forward end thereof. The medial portion also has fourth and fifth eyelets formed therein rearwardly of the third eyelet thereof. An upwardly extending first loop is secured to the upper end of the medial portion rearwardly of the fourth and fifth eyelets thereof. An upwardly extending second loop is secured to the upper end of the medial portion rearwardly of the first loop. An upwardly extending third loop is secured to the upper end of the medial portion rearwardly of the second loop.

Preferably, the lateral and medial portions are of one-piece construction with the lower ends of the lateral and medial portions being connected by a bottom portion which extends below the lower ends of the lateral and medial portions beneath the sole of the shoe.

The ankle brace of this invention also includes a flexible and stretchable body member having upper and lower ends, a lateral side portion, a medial side portion, and a heel portion. The lower end of the lateral side portion of the body member is secured to the lateral portion. The lower end of the medial side portion of the body member is secured to the medial portion. The heel portion of the body member is secured to the rearward ends of the lateral and medial portions.

A flexible and stretchable first strap is provided which has a first end, a second end, an upper end, a lower end and inner and outer sides. The lower end of the first strap is secured to the upper end of the body member so that the first and second ends of the first strap extend forwardly from the body member. Means is provided for selectively connecting the first and second ends of the first strap member together so that the first strap member extends around the ankle of the wearer. An elongated second strap, having first and second ends, is secured to the outer side of the first strap.

A downwardly extending first loop is secured to the second strap at the first end thereof. A downwardly extending second loop is secured to the second strap rearwardly of the first loop thereof. A downwardly extending third loop is secured to the second strap at the second end thereof. A downwardly extending fourth loop is secured to the second strap at the second end thereof rearwardly of the third loop. A downwardly extending fifth loop is secured to the second strap rearwardly of the fourth loop.

The ankle brace of this invention includes a flexible and stretchable lateral tensioning cord having first and second ends. A first end of the lateral tensioning cord is fixed to the inner side of the lateral portion and extends outwardly therefrom through the fourth eyelet of the lateral portion. The lateral tensioning cord extends from its first end and interconnects the first, second and third loops of the lateral portion with the loops extending downwardly from the lateral side of the body member. The second end of the lateral tensioning cord extends through the fifth eyelet of the lateral portion and is secured to the inner side of the lateral portion.

A flexible and stretchable medial tensioning cord is also provided having first and second ends with the first end of the medial tensioning cord being fixed to the inner side of the medial portion. The medial tensioning cord extends outwardly through the fourth eyelet of the medial portion. The medial tensioning cord then interconnects the first, second and third loops which extend upwardly from the medial portion and the first and second loops which extend downwardly from the first strap. The second end of the medial tensioning cord extends inwardly through the fifth eyelet of the medial portion and is secured to the inner side of the medial portion.

The ankle brace of this invention also includes a first loop member having an eyelet formed therein. The lateral tensioning cord extends through the first loop member. A medial loop member is also provided which has an eyelet formed therein. The medial loop member has the medial tensioning cord extending therethrough.

The shoe lace of the shoe extends through the first, second and third eyelets of the lateral portion and extends through the first, second and third eyelets of the medial portion. One end of the shoe lace also extends through the eyelet of the first loop member. The other end of the shoe lace extends through the eyelet of the second loop member. The shoe lace may be drawn tightly and secured. The tightening of the shoe lace affects the tension within the lateral and medial tensioning cords.

It is therefore a principal object of the invention to provide an improved ankle brace.

A further object of the invention is to provide an ankle brace for use with a cleated athletic shoe which permits the wearer's ankle to move through its normal range of motion but which yieldably prevents the ankle from moving beyond its normal range of motion thereby protecting the ankle.

A further object of the invention is to provide an ankle brace of the type described which does not interfere with the normal movement of the person's ankle.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
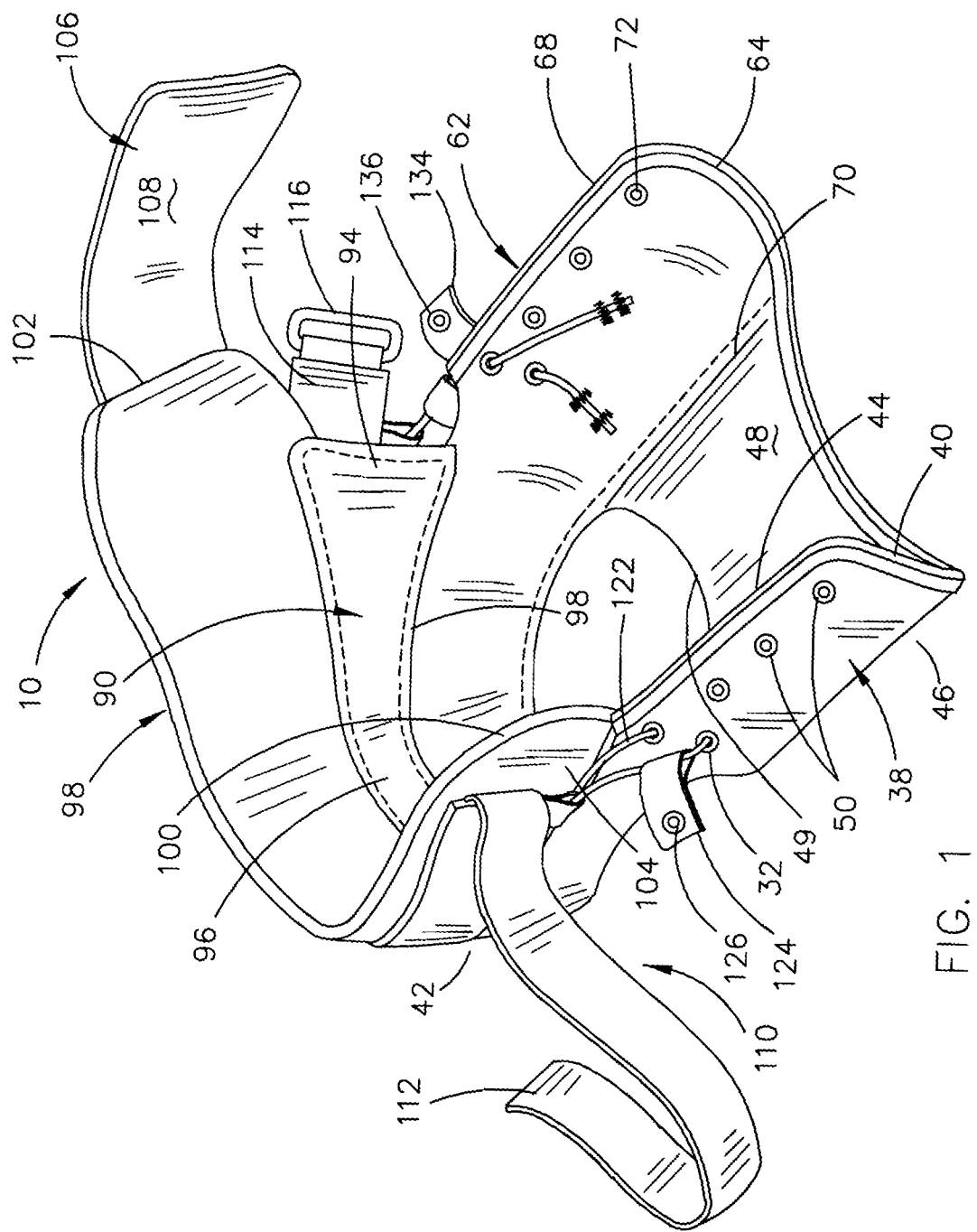
FIG. 1 is a perspective view of the ankle brace of this invention.
Figure 2:
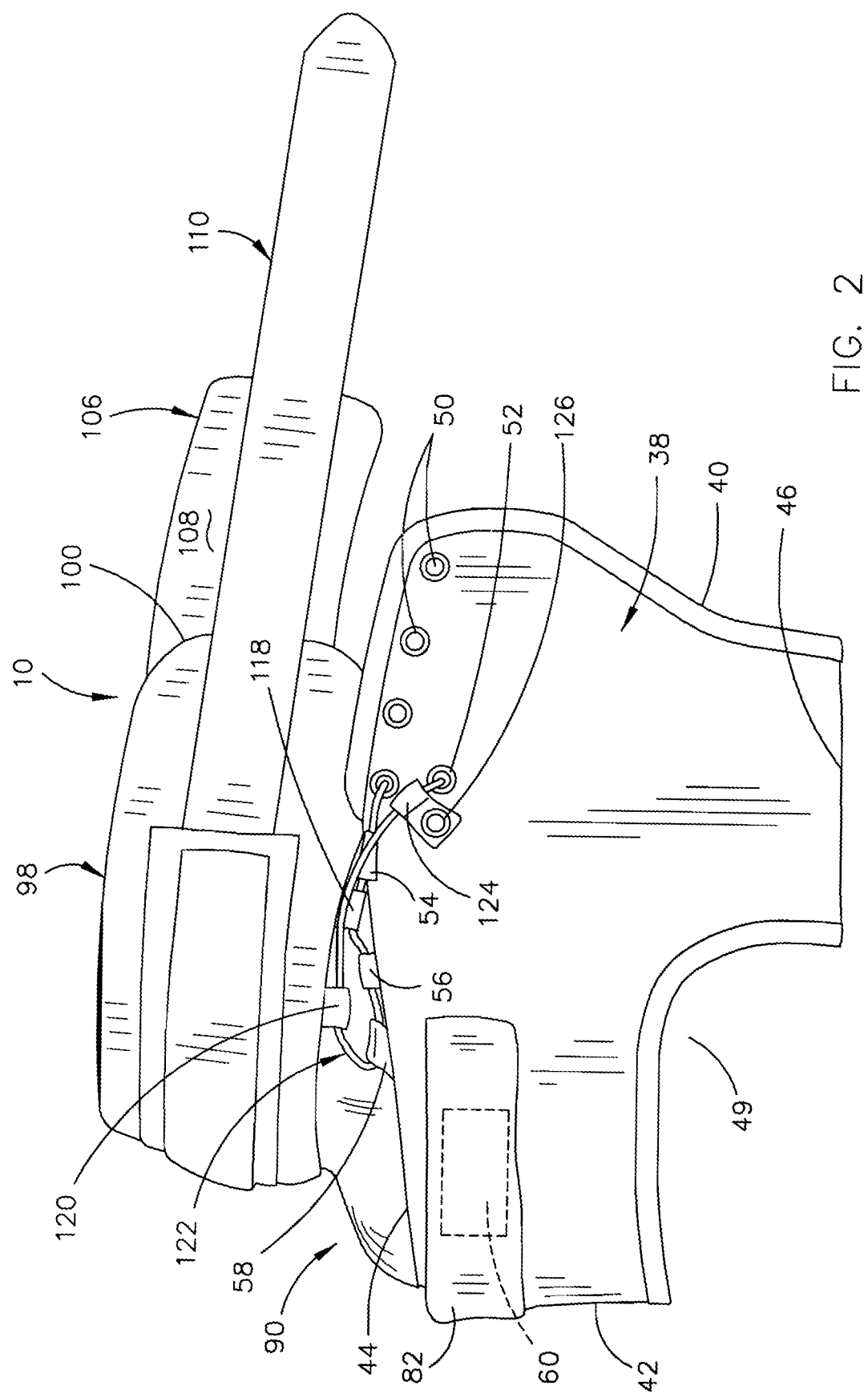
FIG. 2 is a lateral side view of the ankle brace of this invention.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The ankle brace of this invention is referred to generally by the reference numeral 10. Ankle brace 10 is designed to be attached to an athletic shoe 12 having a sole 14 with an underside 16 and an upper part 18. A plurality of cleats 20 extend downwardly from the underside 16 of sole 14. Upper part 18 has a lacing closure structure 22 having a lower end 24 and an upper end 26. Lacing closure structure 22 has a plurality of eyelets, grommets or lace openings 28 designed to receive a shoelace 30 in conventional fashion. Shoe 12 will be described as having a lateral side 32, a medial side 34 and a heel counter 36.

Ankle brace 10 includes a lateral portion 38 having a forward end 40, a rearward end 42, an upper end 44 and a lower end 46. The numeral 48 refers to a bottom member of ankle brace 10 which has one side secured to lateral portion 48 by stitching or the like and which extends below sole 14 as will be described in detail hereinafter. Bottom member 48 has a cut-out portion 49 formed therein at its rearward end. Lateral portion 48 is comprised of a flexible, non-stretchable material such as polyester. The upper forward end of lateral portion 38 has a plurality of spaced-apart grommets or eyelets 50 formed therein. Preferably, four eyelets 50 are formed in lateral portion 38. A grommet or eyelet 52 is formed in lateral portion 38 below the rearward most grommet or eyelet 50.

Loops 54, 56 and 58 are secured to the upper end 44 of lateral portion 38 rearwardly of the rearward most eyelet 50. A strip 60 of hook fasteners is secured to lateral portion 38 at the rearward end 42 thereof.

Ankle brace 10 also includes a medial portion 62 having a forward end 64, a rearward end 66, an upper end 68 and a lower end 70. One end of bottom member 48 is joined to the lower end 70 of medial portion 62. It should be noted that bottom member 48 could be integrally formed with either lateral portion 38 or medial portion 62. Medial portion 62 is also comprised of a flexible, non-stretchable material such as polyester. The upper forward end of medial portion 62 has a plurality of spaced-apart grommets or eyelets 72 formed therein. Preferably, four eyelets 72 are formed in medial portion 62. A grommet or eyelet 74 is formed in medial portion 62 below the rearward most eyelet 72.

Figure 5:
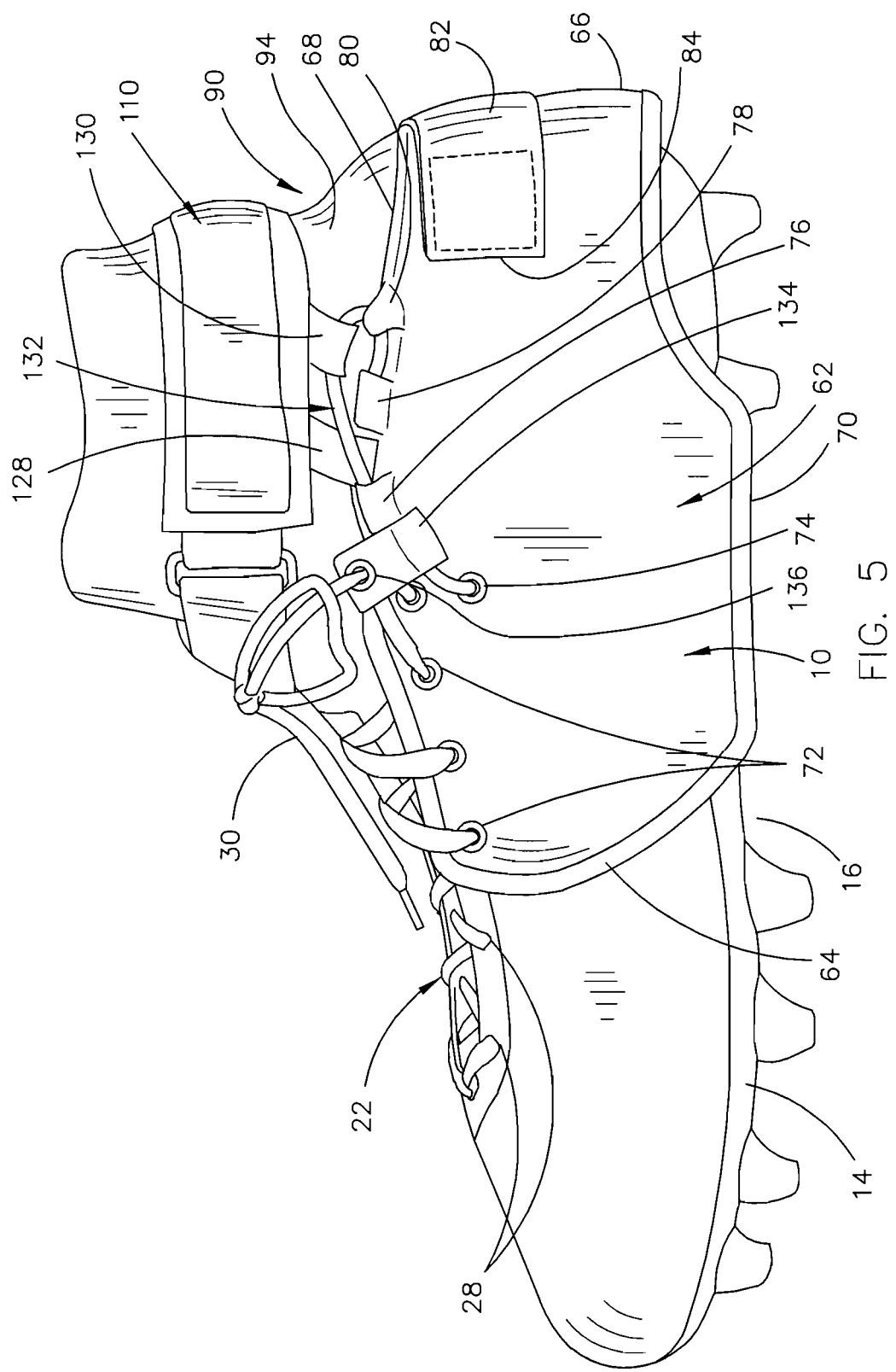
FIG. 5 is a medial side view illustrating the ankle brace of this invention mounted on an athletic shoe.

Loops 76, 78 and 80 are secured to the upper end 68 of medial portion 62 as seen in FIG. 5. An elongated strap 82 has its end 84 fixedly secured to the rearward end of medial portion 62 by stitching as seen in FIG. 5. The other end of strap 82 has loop fasteners 86 secured to the inner side thereof which are adapted to be adjustably received by the hook fasteners on strip 60. In some cases, the strap 82 may be omitted. The rearward end of lateral portion 38 may be secured to the rearward end of medial portion 62 by stitching or the like. Further, the rearward ends of lateral portion 38 and medial portion 62 may be spaced-apart as illustrated in the co-pending application.

The numeral 90 refers to a flexible and stretchable body member preferably comprised of neoprene or the like which is secured to lateral portion 38 and medial portion 62 as will now be described. Body member 90 includes a lateral side portion 92, a medial side portion 94 and a heel portion if the rearward ends of lateral portion 38 and medial portion 62 are spaced-apart. The lower end of lateral side portion 92 of body member 90 is secured to the upper end 44 of lateral portion 38 by stitching or the like. The lower end of medial side portion 94 is secured to the upper end of medial portion 62 by stitching or the like. If the rearward ends of lateral portion 38 and medial portion 62 are separated, the heel portion of body member 90 is positioned between the rearward ends of lateral portion 38 and medial portion 62 and secured thereto.

The numeral 98 refers to an elongated flexible strap having ends 100 and 102. The lower end of strap 98 is secured to the upper end of body member 90 by stitching or the like. The outer side of strap 98 has loop fasteners 104 provided thereon. A strap 106 has its inner end secured to end 102 of strap 98. The inner side of strap 106 has hook fasteners 108 provided thereon. An elongated strap 110 is secured to the outer side of strap 98 and includes ends 112 and 114. A ring 116 is secured to end 114 of strap 110. The outer side of end 112 of strap 110 has hook fasteners thereon.

Figure 3:
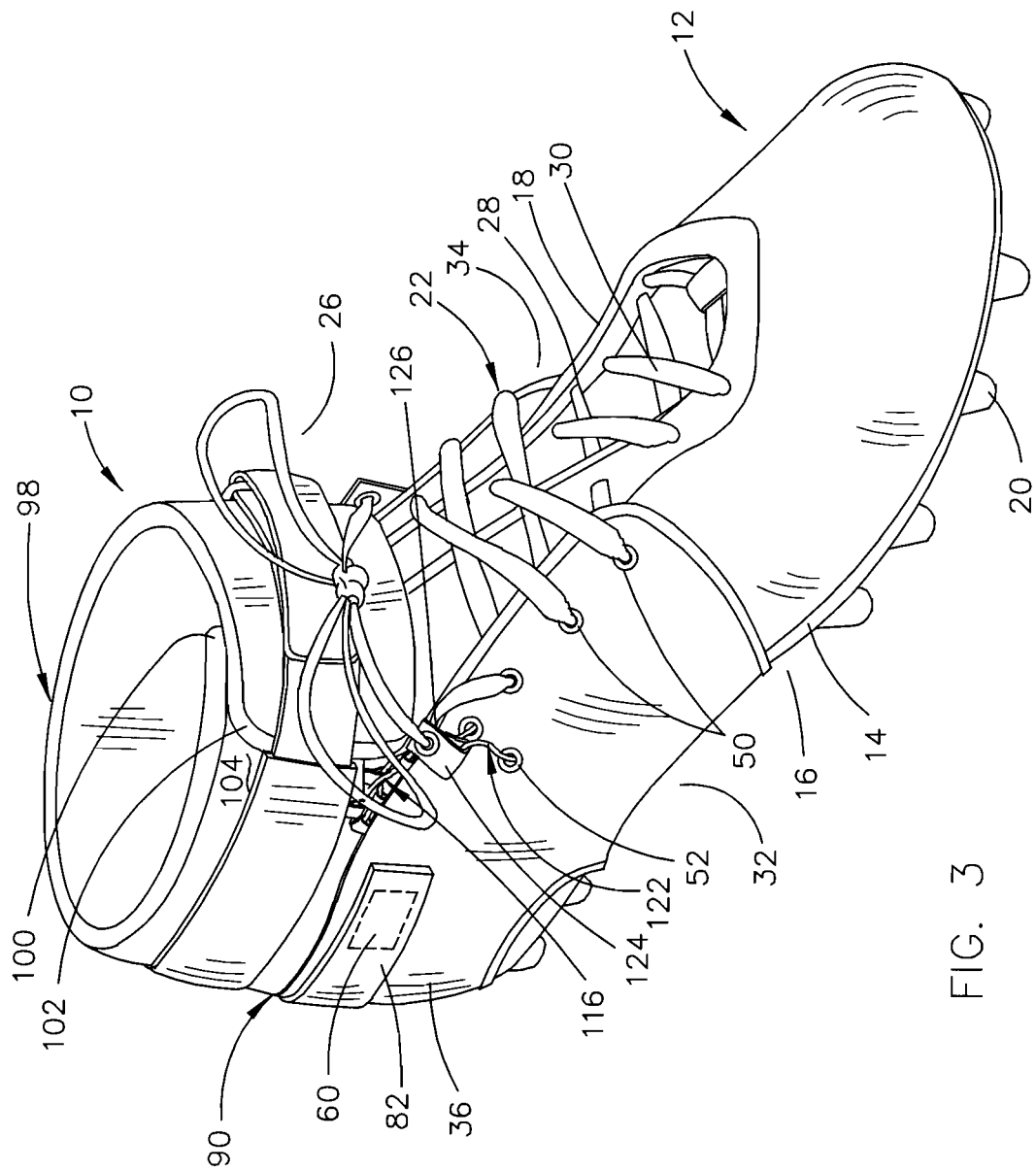
FIG. 3 is a perspective view illustrating the ankle brace of this invention mounted on an athletic shoe.
Figure 4:
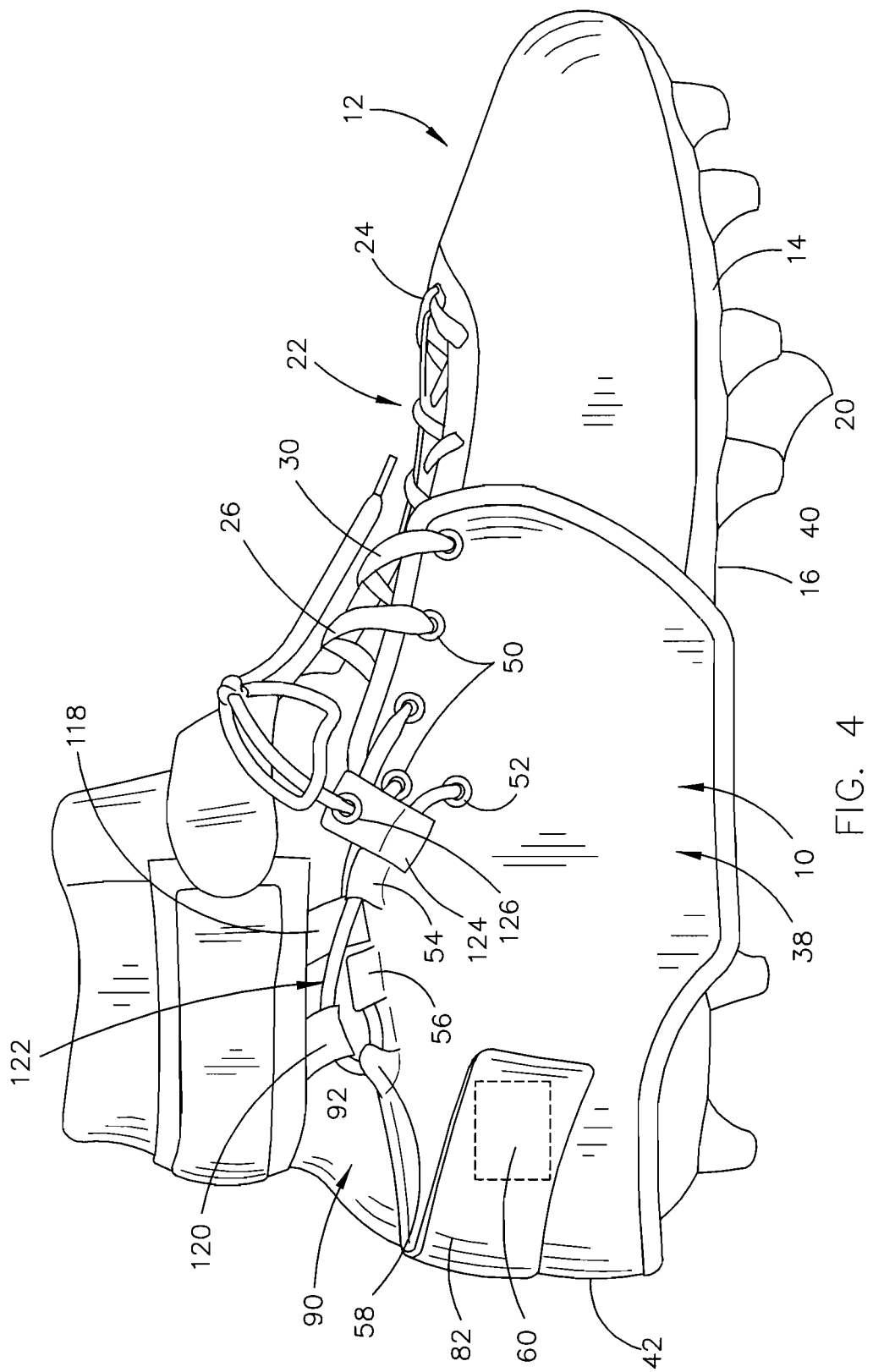
FIG. 4 is a lateral side view illustrating the ankle brace of this invention mounted on an athletic shoe.

Loops 118 and 120 are secured to the lower end of the lateral side of strap 98. The numeral 122 refers to an elastic lateral tensioning cord which yieldably interconnects the upper end of lateral portion 36 to the strap 110 or the strap 98. One end of tensioning cord 122 passes through the rearward most eyelet 50 and the other end of tensioning cord 122 passes through eyelet 52. The ends of tensioning cord 122 are secured to the inner side of lateral portion 38. As seen, the tensioning cord 122 passes through loops 54, 56, 58 and loops 118 and 120. A loop 124 is slidably mounted on tensioning cord 122 as seen in FIG. 3. Loop 124 includes an eyelet 126.

Loops 128 and 130 are secured to the lower end of the medial side of strap 98. The numeral 132 refers to an elastic medial tensioning cord which yieldably interconnects the upper end of medial portion 62 to the strap 110 or the strap 98. One end of tensioning cord 132 passes through the rearmost eyelet 72 and the other end of cord 132 passes through eyelet 74. The ends of tensioning cord 132 are secured to the inner side of medial portion 62. As seen, the tensioning cord 132 passes through loops 76, 78, 80 and loops 128 and 130. A loop 134 is slidably mounted on tensioning cord 132 as seen in FIG. 5. The loop 134 includes an eyelet 136.

Figure 6:
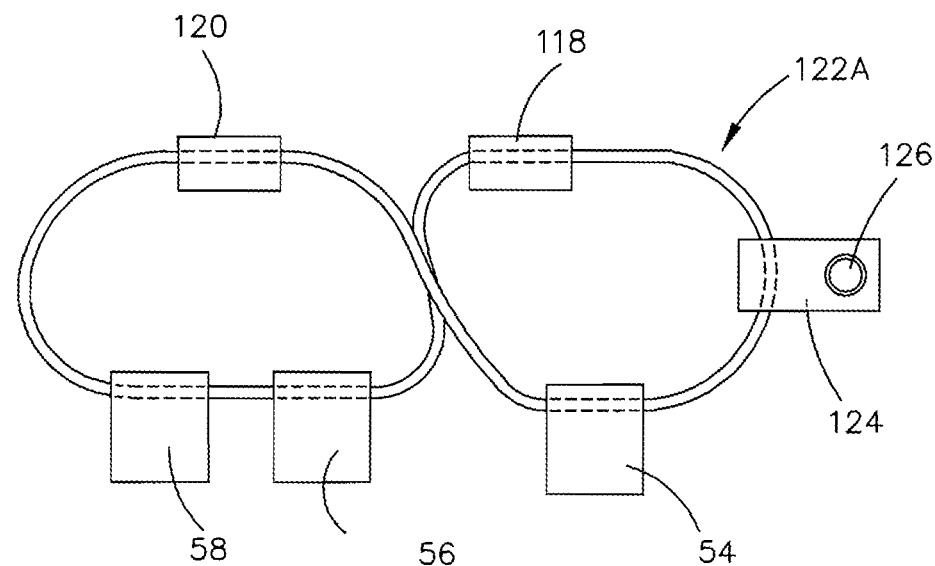
FIG. 6 is a schematic view which illustrates a lateral tensioning O-ring rather than a lateral tensioning cord.
Figure 7:
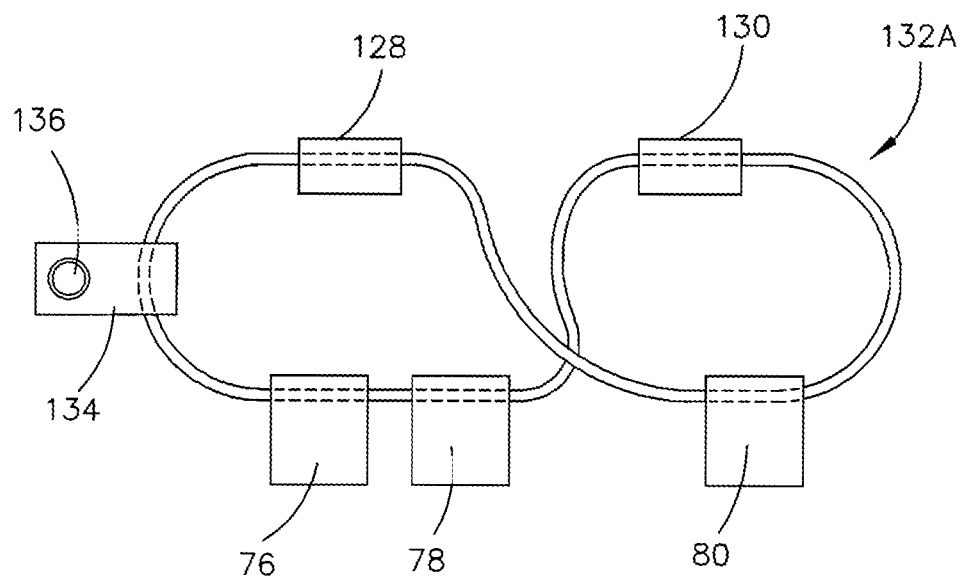
FIG. 7 is a schematic view which illustrates a medial tensioning O-ring rather than a medial tensioning cord.

Although the drawings illustrate that the ends of tensioning cord 122 are secured to the inner side of lateral portion 38, the tensioning cord 122 could be replaced with an elastic tensioning O-ring 122A as seen in FIG. 6 which yieldably interconnects the loops 118 and 120 with the loops 54, 56 and 58 and which has the loop 124 slidably mounted thereon. Similarly, although the drawings illustrate that the ends of tensioning cord 132 are secured to the inner side of medial portion 62, the tensioning cord 132 could be replaced with an elastic tensioning O-ring 132A as seen in FIG. 7 which yieldably interconnects the loops 128 and 130 with the loops 76, 78 and 80 and which has the loop 134 slidably mounted thereon.

In use, the brace 10 is positioned on the shoe 12 as seen in the drawings. The shoe lace 30 is threaded through some of the lower lace openings or eyelets 28 and through at least some of the eyelets 50 of lateral portion 38 and some of the eyelets 72 of medial portion 62. The shoe lace 30 is then threaded through the remaining eyelets 28. One end of the shoe lace 30 is threaded through eyelet 126 of loop 124. The other end of shoe lace 30 is threaded through eyelet 136 of loop 134. The shoe lace 30 is then drawn tightly which causes the tensioning cords 122 and 132 to be placed in the desired tension by way of the loops 124 and 134. The shoe lace 30 is then tied. Strap 106 is then secured to strap 98 at end 100 thereof. End 112 of strap 110 is then inserted through buckle 116 and folded upon itself and secured.

The ankle brace 10 permits the ankle of the person to move through its natural range of motion either laterally, medially, fore and aft. When the ankle moves toward the end of its normal range of motion, the tensioning cords 122 and 132 resist further motion to protect the ankle. Ankle support is also provided by the flexible and stretchable body member 90 which enables the person's ankle to move through its normal range of motion.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace for use with an athletic shoe having a sole with a lower cleated surface, a lateral side and a medial side, an upper part with an upper end, a lacing closure, with upper and lower ends, including a plurality of spaced-apart pairs of eyelets adapted to have a shoe lace, having first and second ends, threaded therein, comprising:

a lateral portion having an upper end, a lower end, a forward end, a rearward end, an outer side and an inner side;

said upper end of said lateral portion having a plurality of spaced-apart first eyelets formed therein at said forward end thereof;

a plurality of spaced-apart lateral loops secured to said lateral portion at said upper end of said lateral portion rearwardly of said plurality of spaced-apart first eyelets of said lateral portion and which extend upwardly from said lateral portion;

said lateral portion being selectively removably positioned adjacent the lateral side of the upper part of the shoe:

a medial portion having an upper end, a lower end, a forward end, a rearward end, an outer side and an inner side;

said upper end of said medial portion having a plurality of spaced-apart first eyelets formed therein at said forward end thereof;

a plurality of spaced-apart medial loops secured to said medial portion rearwardly of said plurality of spaced-apart first eyelets of said medial portion and which extend upwardly from said medial portion;

said lower ends of said lateral and medial portions being joined together by means of a bottom member which extends beneath the sole of the shoe;

a flexible body member including a lateral side portion, with upper and lower ends, and a medial side portion, with upper and lower ends;

said lower end of said lateral side portion of said flexible body member being secured to said upper end of said lateral portion;

said lower end of said medial side portion of said flexible body member being secured to said upper end of said medial portion;

a flexible first strap having a first end, a second end, an upper end, a lower end, and inner and outer sides;

said lower end of said flexible first strap being secured to said upper end of said flexible body member so that said first and second ends of said flexible first strap extend forwardly from said flexible body member;

said flexible first strap configured to extend around the ankle of the wearer;
said flexible first strap including means to secure said first and second ends thereof together around the ankle of the wearer;
an elongated and flexible second strap having a first end, a second end, an inner side and an outer side;
said elongated and flexible second strap being secured to said outer side of said flexible first strap so as to extend at least partially therearound;
a plurality of lateral loops operatively secured to said elongated and flexible second strap and which extend downwardly therefrom;
a plurality of medial loops operatively secured to said elongated and flexible second strap and which extend downwardly therefrom;
a flexible and stretchable lateral tensioning member;
said flexible and stretchable lateral tensioning member interconnecting said plurality of spaced-apart lateral loops of said lateral portion with said plurality of lateral loops of said elongated and flexible second strap;
a flexible and stretchable medial tensioning member;
said flexible and stretchable medial tensioning member interconnecting said plurality of spaced-apart medial loops of said medial portion with said medial loops of said elongated and flexible second strap;
a lateral tensioning loop slidably embracing said flexible and stretchable lateral tensioning member and which has an eyelet formed therein;
a medial tensioning loop slidably embracing said flexible and stretchable medial tensioning member and which has an eyelet formed therein;
the first end of the shoe lace being threaded through some of the eyelets of the shoe and through said plurality of spaced-apart first eyelets of said lateral portion with the first end of the shoe lace being threaded through said eyelet of said lateral tensioning loop;
the second end of the shoe lace being threaded through some of the eyelets of the shoe and through some of the plurality of spaced-apart first eyelets of said medial portion with the second end of the shoe lace being threaded through said eyelet of said medial tensioning loop; and
the first and second ends of the shoe lace being tied together.

2. The ankle brace of claim 1 wherein said flexible and stretchable lateral tensioning member comprises an O-ring and wherein said flexible and stretchable medial tensioning member comprises an O-ring.

3. The ankle brace of claim 1 wherein said flexible and stretchable lateral tensioning member comprises an elongated cord and wherein said flexible and stretchable medial tensioning member comprises an elongated cord.

* * * * *